(12) United States Patent
Saadat et al.

(10) Patent No.: US 6,363,938 B2
(45) Date of Patent: Apr. 2, 2002

(54) METHODS AND APPARATUS FOR PERFUSING TISSUE AND/OR STIMULATING REVASCULARIZATION AND TISSUE GROWTH

(75) Inventors: Vahid Saadat, Redwood Shores; James Kermode, Sunnyvale; John H. Ream, San Jose, all of CA (US)

(73) Assignee: Angiotrax, Inc., Sunnyvale, CA (US)

( * ) Notice: Subject to any disclaimer, the term of this patent is extended or adjusted under 35 U.S.C. 154(b) by 0 days.

(21) Appl. No.: 09/219,092

(22) Filed: Dec. 22, 1998

(51) Int. Cl.$^7$ .............................................. A61B 19/00
(52) U.S. Cl. ...................... 128/898; 623/1.11; 623/1.15
(58) Field of Search .................. 128/898; 606/192–200, 606/167, 185, 109; 604/500, 507, 508, 104–109; 623/1.1, 1.11, 1.15, 1.16, 1.23, 1.39

(56) References Cited

U.S. PATENT DOCUMENTS

| | | | |
|---|---|---|---|
| 4,658,817 A | 4/1987 | Hardy | 128/303 |
| 4,813,930 A | 3/1989 | Elliott | 606/53 |
| 5,059,211 A | 10/1991 | Stack et al. | 606/198 |
| 5,244,460 A | * 9/1993 | Unger et al. | 604/53 |
| 5,342,348 A | * 8/1994 | Kaplan | 623/13 |
| 5,380,316 A | 1/1995 | Aita et al. | 606/7 |
| 5,389,096 A | 2/1995 | Aita et al. | 606/15 |
| 5,554,152 A | 9/1996 | Aita et al. | 606/7 |
| 5,591,159 A | 1/1997 | Taheri | 606/15 |
| 5,617,878 A | 4/1997 | Taheri | 128/898 |
| 5,681,345 A | 10/1997 | Euteneuer | 606/198 |
| 5,707,385 A | 1/1998 | Williams | 606/192 |
| 5,899,917 A | * 5/1999 | Edwards et al. | 606/195 |
| 5,910,150 A | 6/1999 | Saadat | 606/159 |
| 5,944,710 A | * 8/1999 | Dev et al. | 604/500 |

FOREIGN PATENT DOCUMENTS

| | | |
|---|---|---|
| FR | 2466994 | 10/1979 |
| WO | WO 97/27735 | 8/1997 |
| WO | WO 97/31577 | 9/1997 |
| WO | WO 97/32551 | 9/1997 |

OTHER PUBLICATIONS

Fleischer et al., "One–Month Histologic Response of Transmyocardial Laser Channels With Molecular Intervention", *Ann. Soc. Thoracic Surg.*, 62:1051–58 (1996).

Nimni, "Polypeptide Growth Factors: Targeted Delivery Systems", *Biomaterials*, 18:1–25 (1997).

Schumacher et al., "Induction of Neoangiogenesis in Ischemic Myocardium by Human Growth Factors", *Circulation*, 97:645–650 (1998).

* cited by examiner

Primary Examiner—Glenn K. Dawson
(74) Attorney, Agent, or Firm—Fish & Neave; Nicola A. Pisano (57) ABSTRACT

Apparatus and methods are provided for forming a channel in an organ or vessel to enhance perfusion therein. The apparatus may include a bioactive agent to stimulate tissue growth and vascularization in tissue adjacent to the channel. The apparatus includes a stent, suitable for percutaneous or intraoperative placement, that includes a tubular member having a plurality of tines, barbs, ribs or other structure to secure the stent at a desired position within tissue.

6 Claims, 5 Drawing Sheets

METHODS AND APPARATUS FOR
PERFUSING TISSUE AND/OR
STIMULATING REVASCULARIZATION AND
TISSUE GROWTH

FIELD OF THE INVENTION

The present invention relates to apparatus and methods for perfusing myocardial tissue and stimulating tissue growth and revascularization in a vessel or organ. More particularly, the present invention relates to a device that may be implanted in a vessel or organ, such as the heart, to form a channel for perfusing tissue, and may include a bioactive agent to stimulate tissue regeneration and vascularization.

BACKGROUND OF THE INVENTION

A leading cause of death in the United States and the world today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery replaced with a native artery harvested elsewhere or a synthetic graft, has been the conventional treatment for coronary artery disease for the last thirty years. Such surgery creates significant trauma to the patient, requires long recuperation time, and poses serious risks of mortality. In addition, experience has shown that the bypass vessel or graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then dilated to compress the plaque lining the artery to restore patency to the vessel. Atherectomy involves using a catheter having a mechanical cutting tip or a laser to cut (or ablate) a passage through the blockage. Such methods have drawbacks, however, ranging from re-blockage of vessels dilated by angioplasty, to catastrophic rupture or dissection of the vessel during atherectomy. Moreover, these methods only may be used for that fraction of the patient population that have a few, easily accessible blockages. Neither technique is suitable for the treatment of diffuse atherosclerosis.

A more recent experimental technique for treating ischemia uses recombinant protein therapy to induce neoangiogenesis in the human heart. Schumacher et al., *Induction of Neoangiogenesis in Ischemic Myocardium by Human Growth Factors*, 97 Circulation 645 (1998) report the results of a study in which fibroblast growth factor (FGF-I), a human growth factor obtained through genetic engineering, was injected into the myocardium of 20 patients suffering from stenosis of the internal mammary artery/left anterior descending coronary artery. Within 4 days after application of FGF-I, new capillary vessels radiated outward from the injection point. Although the results of the study appear encouraging, it is unclear whether growth factor therapy alone will be able to treat occlusions of the greater coronary vessels.

Another recent technique that holds promise of treating a large percentage of the patient population, including those patients suffering from diffuse atherosclerosis, is referred to as transmyocardial revascularization (TMR). In this method, a series of channels are formed in the left ventricular wall of the heart. The channels may be transmural (i.e., from the epicardium to the endocardium), or intramural (for example, from the endocardium and terminating in the myocardium).

Typically, between 15 and 40 channels about 1 mm in diameter and up to 3.0 cm deep are formed with a laser in the wall of the left ventricle to perfuse the heart muscle with blood coming directly from the inside of the left ventricle, rather than from the coronary arteries. Apparatus and methods have been proposed to create these channels both percutaneously and intraoperatively (i.e., with the chest opened).

U.S. Pat. Nos. 5,380,316 and 5,554,152 to Aita et al. describe intraoperative laser apparatus for forming channels extending from the epicardium to the endocardium. The laser includes an optical wave guide that is held against the patient's heart. Several pulses of the laser are required to form a transmural channel by ablation. U.S. Pat. No. 5,389,096 to Aita et al. describes a catheter-based laser system for performing TMR percutaneously, i.e., from within the left ventricle. U.S. Pat. No. 4,658,817 to Hardy describes a laser-based system for intraoperatively performing TMR that includes a needle portion for perforating an outer portion of the tissue, and a laser for ablating the inner portion.

U.S. Pat. No. 5,591,159 to Taheri describes a mechanical catheter-based apparatus for performing TMR involving a catheter having an end effector formed from a plurality of spring-loaded needles. The catheter first is positioned percutaneously within the left ventricle. Then, a plunger is released so that the needles are thrust into the endocardium, and the needles are withdrawn, thus forming small channels that extend into the myocardium. The patent suggests that the needles may be withdrawn and advanced repeatedly at different locations under fluoroscopic guidance.

Although TMR has been observed to benefit many patients, researchers do not agree upon the mechanism by which TMR provides therapeutic benefits. One theory proposes that TMR channels remain patent for long periods of time, and provide a path by which oxygenated blood perfuses the myocardium. Relatively recent histological studies, however, indicate that TMR channels may close within a short time following the procedure. Fleischer et al., *One-Month Histologic Response Of Transmyocardial Laser Channels With Molecular Intervention*, 62 Ann. Soc. Thoracic Surg. 1051–58 (1996), describe a study that evaluated the histologic changes associated with laser TMR in a 1-month nonischemic porcine model, and report that the researchers were unable to demonstrate channel patency 28 days after TMR.

Patent Cooperation Treaty Publication No. WO 97/32551 describes apparatus for performing TMR that creates a TMR channel and then implants a stent in the channel to maintain channel patency. For intraoperative TMR, a needle obturator first creates a channel in the myocardium, and a stent is then inserted in the channel. For percutaneous TMR, a drill at the end of a catheter first forms channels in the myocardium, and then a stent is inserted into the channel.

The foregoing apparatus have the disadvantage of requiring separate needle obturators or drills that must first create the channel before the stent is inserted into the myocardium. It therefore would be desirable to provide TMR stent apparatus to maintain channel patency, but that does not require a separate channel forming device.

An alternative theory regarding the means by which TMR provides therapeutic benefits proposes that in addition to channel formation and patency, myocardial neovascularization outside the channel area following channel formation is also important. To investigate this theory, researchers have combined the techniques of TMR and neoangiogenesis to study the use of gene therapy to promote blood vessel growth in the tissue surrounding laser TMR channels. In one study, researchers intraoperatively administered a single dose of vascular endothelial growth factor (VEGF) within the channels formed by laser TMR. While no significant increase in myocardial vascularity was observed, it was hypothesized that increased residency of VEGF may be required to stimulate angiogenesis.

Because the therapeutic benefit of TMR may result from a combination of channel patency and myocardial angiogenesis outside the channel area, it also would be desirable to provide methods and apparatus that maintain TMR channel patency and stimulate neoangiogenesis in the myocardial tissue surrounding TMR channels.

SUMMARY OF THE INVENTION

In view of the foregoing, it is an object of this invention to provide apparatus and methods for simultaneously forming a channel within a vessel or organ and introducing a stent to retain that channel patent, without requiring the use of a separate channel forming device.

It is a further object of the present invention to provide apparatus and methods comprising an implantable device that maintains channel patency and that may include a bioactive agent to stimulate tissue growth and revascularization.

It is a further object of this invention to provide apparatus and methods for implanting a series of stents at a plurality of tissue locations without having to repeatedly reload the stent delivery system.

These and other objects of the present invention are accomplished by providing a stent that simultaneously creates a channel in a vessel or organ and becomes implanted therein, to maintain the patency of the channel. The stent preferably includes a first end region that forms an intramural channel, and means for retaining the stent within the channel, such as an expandable mesh portion, barbs, tines or ribs, so that it is not dislodged by heart wall motion. The stent may comprise a bioactive agent to stimulate tissue regeneration and/or vascularization in tissue adjacent to the stent following implantation.

In one embodiment, the stent is configured from implantation in the left ventricle to promote perfusion and angiogenesis. The stent preferably includes a bore having an inlet, an outlet, and a plurality of apertures that extend from the bore to an exterior lateral surface of the stent. The stent may be fabricated from a bioresorbable material impregnated with a bioactive agent, such as an angiogenic growth factor, or alternatively, from nonresorbable material coated with a layer of a bioactive agent.

The stent optionally may include a second end region having means for securing the stent against movement, such as a flange, or one or more self-expanding barbs or tines. In other embodiments the stent may comprise a series of conical ribs or conical sections formed of a bioresorbable material impregnated with a bioactive agent, or may include bioactive agents that vary as a function of length or thickness of the stent. In yet other embodiments, the stent may comprise a rod of bioresorbable material that is implanted intraoperatively adjacent to a constricted artery to stimulate revascularization.

Delivery systems and methods of use are also provided for simultaneously forming a channel in a vessel or organ, and implanting the stent.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention relates generally to apparatus and methods for forming a channel in a wall of a vessel or organ and implanting a stent that perfuses the tissue. In addition, the stent may include a bioactive agent to stimulate revascularization and/or tissue growth, such as vascular endothelial growth factor (VEGF), e.g., VEGF165 or VEGF121, fibroblast growth factor, type I (FGF-I) or type II (FGF-II), PDGF, MCPI, platelet components, cardio myocytes or endothelial cells. The following written description describes illustrative embodiments of the present invention, delivery systems for use therewith, and describes operation of such systems. Features suitable for use in further alternative embodiments also are set forth.

Although the invention is described hereinafter as particularly useful in the emerging field of transmyocardial revascularization, methods and apparatus in accordance with the present invention advantageously may be used for perfusing or stimulating tissue regeneration in other organs and vessels. In addition, although the present invention describes using bioactive agents, such as angiogenic growth factors, for stimulating myocardial revascularization, the methods and apparatus of the present invention also may be used for providing other drugs, proteins and bioactive agents.

Figures 1, 2, 3:
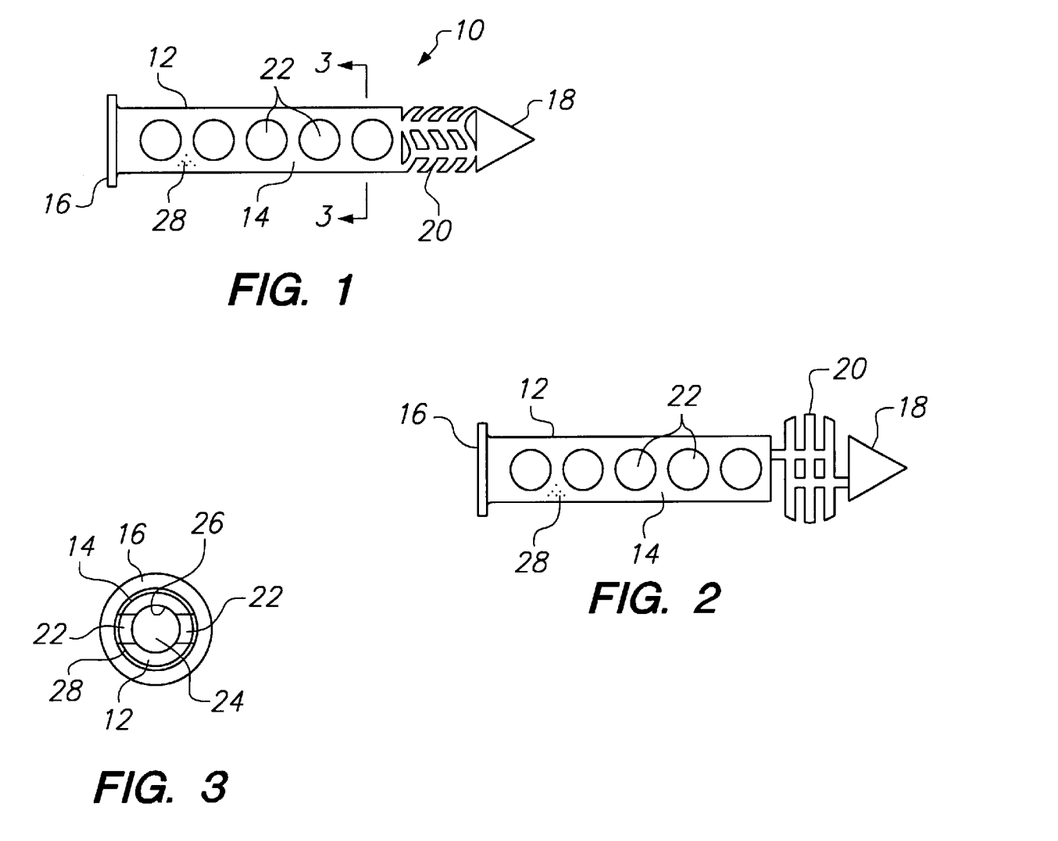
FIG. 1 is a side view of a first embodiment of a stent in its unexpanded state constructed in accordance with the present invention.
FIG. 2 is a side view of the stent of FIG. 1 in its expanded state.
FIG. 3 is a sectional view along line 3—3 of FIG. 1.

Referring to FIGS. 1 and 2, illustrative apparatus 10 constructed in accordance with the present invention is described. In FIG. 1, stent 10 comprises tubular body 12, having exterior surface 14, flange 16 extending radially outward from exterior surface 14, sharpened tip 18, and expandable mesh structure 20. Body 12 includes a bore and a plurality of apertures 22 that extend from the bore to exterior lateral surface 14 of the stent. In FIG. 2 stent 10 is shown with expandable mesh structure 20 in its expanded state, for example, as the stent may be implanted in the myocardium of the left ventricle.

Referring now also to FIG. 3, the internal structure of stent 10 is described. Bore 24 extends from flange 16 to sharpened tip 18, and permits fluid communication between the interior and exterior surface 14 of the stent 10 via apertures 22. In particular, blood from the left ventricle enters bore 24 through an inlet at flange 16, flows through the bore toward sharpened tip 18, and exits through apertures 22 to supply blood to tissue within which the stent is implanted. Although FIG. 3 illustrates symmetrically opposed apertures 22, it will be understood that one or more apertures may be included without departing from the principles of the present invention.

Tubular body 12 may be fabricated from metal, plastic, or a bioresorbable material. Suitable metals include, for example, stainless steel, nickel, nickel titanium, and tantalum, whereas suitable plastic materials include polyetheretherketone (PEEK), polysufone, and polyimide. Hydroxyapatite, polyglycolic acid and polylactic acid are examples of bioresorbable materials that may be advantageously used to construct tubular body 12.

In accordance with one aspect of the present invention, stent 10 may be coated on either interior surface 26 or exterior surface 14 with a layer of bioactive agent 28, such as a drug or angiogenic growth factor. Suitable growth factors may comprise, for example, vascular endothelial growth factor (VEGF), e.g., VEGF165 or VEGF121, fibroblast growth factor, type I (FGF-I) or type II (FGF-II), PDGF, MCPI, platelet components, cardio myocytes or endothelial cells.

Applicants expect that if coating 28 is disposed on exterior surface 14 of stent 10, sustained exposure by the tissue to the bioactive agent will stimulate revascularization and/or tissue regeneration in the tissue surrounding the stent. Alternatively, if coating 28 is disposed on interior surface 26 of bore 24, it is expected that the bioactive agent will be dissolved by blood entering bore 24, and carried into tissue surrounding stent 10 through apertures 22. As further alternatives, stent 10 may be constructed from a bioresorbable material that is impregnated with a bioactive agent, or may be constructed from nonresorbable material coated with bioresorbable material that contains a bioactive agent.

Figure 4A:
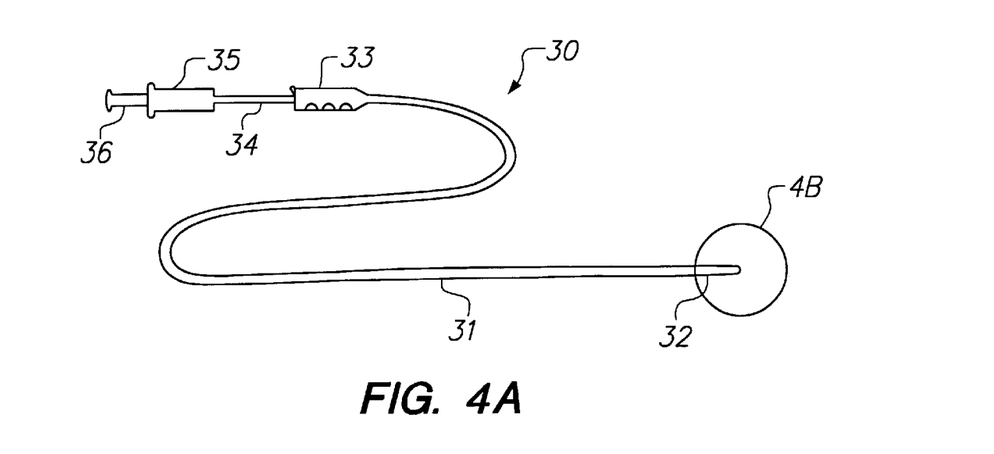
FIGS. 4A and 4B are, respectively, a view of an illustrative delivery system for use in implanting the stent of FIG. 1 and a sectional side view of a distal end of the delivery system of FIG. 4A and the stent of FIG. 1.
Figure 4B:
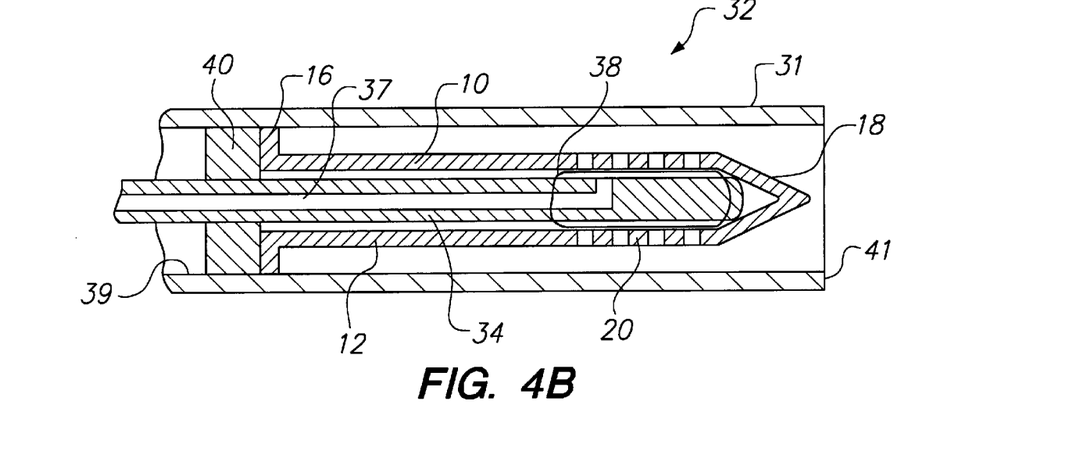

Referring now to FIGS. 4A and 4B, illustrative delivery system 30 for forming a channel in tissue and implanting the stent of FIG. 1 is described. Delivery system 30 includes catheter 31 having distal end 32, first handle portion 33, push tube 34 and second handle portion 35. Second handle portion 35 includes syringe 36, which is coupled through lumen 37 (see FIG. 4B) to balloon element 38 disposed on the distal end of push tube 34.

Delivery system 30 may in addition include a series of stabilization members, such as described in copending commonly assigned U.S. patent application Ser. No. 08/863,877, or U.S. Pat. No. 4,813,930 to Elliott, both of which are incorporated herein by reference. Such stabilization members may be desirable to counteract reaction forces generated during the implantation process as the stent is urged into the tissue.

Push tube 34 is mounted for translation through lumen 39 of catheter 31, and has push block 40 mounted near its distal end. Push block 40 abuts against the proximal face of flange 16 of stent 10. Balloon element 38 is disposed near the distal end of push tube 34 so that when the push tube is inserted within bore 24 of stent 10, the balloon element is disposed within expandable mesh portion 20. Balloon element 38 is inflated via a suitable inflation medium using syringe 36 and lumen 37. Push tube 34 may comprise, for example, a stainless steel hypotube, while balloon 38 preferably is non-compliant or semi-compliant, and may be constructed of polyethyl-tetraphlate, polyurethane or nylon. Balloon 38 is bonded to push tube 34 using techniques that are per se known.

Catheter 31 is of a length suitable for percutaneous transluminal deployment of stent 10, and may be constructed of materials conventionally used in manufacturing catheter systems, such as polyethylene, nylon or polyurethane. Alternatively, delivery system 30 may be made much shorter, for example, if stents 10 are to be implanted intraoperatively, for example, through a surgical opening in the vena cava or aorta.

Delivery system 30 may be percutaneously and transluminally inserted into the left ventricle using techniques that are per se known. During insertion of delivery system 30 to a treatment site, delivery system 30 is manipulated using first handle portion 33, while second handle portion 35 is in the proximal-most position. Once distal endface 41 of catheter 31 has been disposed at an implantation site, for example, as determined by fluoroscopy, second handle portion 35 is translated towards first handle portion 33.

Movement of second handle portion 35 towards first handle portion 33 (which is held stationary) urges push tube 34 in the distal direction. This translation is transmitted to push block 40 mounted on push tube 34, thereby causing stent 10 to extend from within lumen 39 and to pierce and become implanted in the tissue. Forward movement of stent 10 into the myocardium is arrested when flange 16 abuts against the endocardium. Syringe 36 of second handle portion 35 is then actuated to expand balloon element 38, which turn deforms expandable mesh portion 20 to the state shown in FIG. 2, for example, up to two times its original diameter. Syringe 36 is then withdrawn to collapse balloon element 38, and push tube 34 and catheter 31 are withdrawn.

Figure 5:
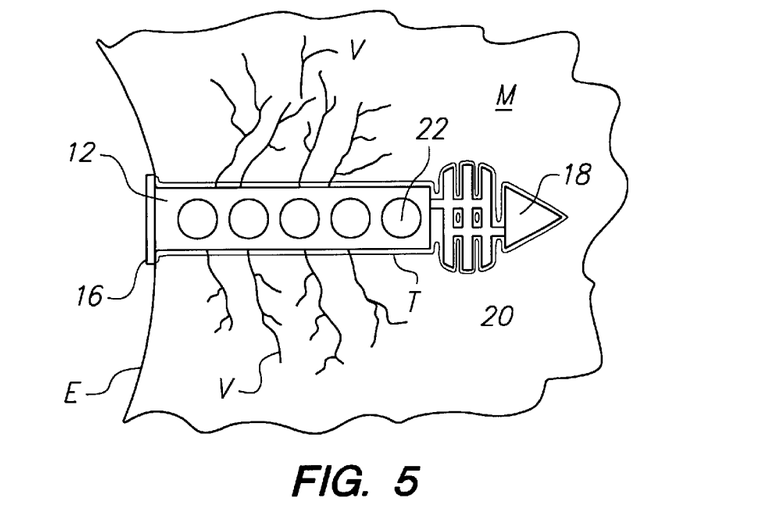
FIG. 5 is a side view of the stent of FIG. 1 at an interval following implantation.

In FIG. 5, stent 10 is described at an interval of time after implantation. As shown in FIG. 5, stent 10 is implanted in myocardium M so that flange 16 abuts against endocardium E, and a plurality of vessels V have formed in a regenerated tissue layer T adjacent to the stent. Expandable mesh portion 20 secures stent 10 within myocardium M, while flange 16 prevents the stent from being urged further into the myocardium due to the rhythmic contraction of the heart. It is expected that bore 24 of stent 10 will preserve the patency of the channel, while apertures 22 will assist in perfusing the newly formed vasculature.

As an alternative to the above-described embodiment, expandable mesh portion 20 of stent 10 may instead be formed of a material, such as nickel-titanium, so that mesh portion 20 self-expands when released from a restraint. Thus, for example, instead of deforming expandable mesh portion 20 using balloon element 38 as described hereinabove, stent 10 may instead be constrained within catheter 31 in a contracted state, and return to an expanded state when it is ejected from lumen 39 of catheter 31 by push tube 34. In this case, the balloon element may be omitted from push tube 34.

Figure 6A:
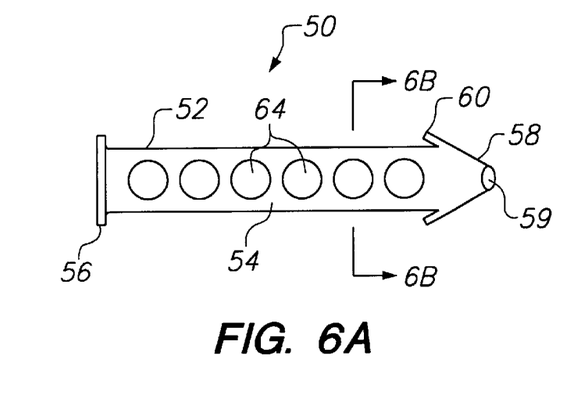
FIGS. 6A and 6B are, respectively, a side view and a sectional view, along line 6B—6B of FIG. 6A, of an alternative embodiment of a stent constructed in accordance with the present invention.
Figure 6B:
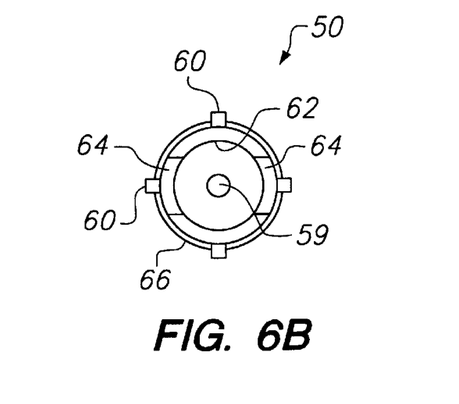

Referring to FIGS. 6A and 6B, another alternative embodiment of the stent of the present invention is described. Stent 50 has tubular body 52, exterior surface 54, flange 56 extending radially outward from exterior surface 54, sharpened tip 58, and barbs 60. Bore 62 extends within stent 50 from flange 56 to sharpened tip 58. Apertures 64 enable bore 62 to communicate with exterior surface 54, thereby permitting fluid communication between the interior and exterior of stent 50. Optionally, stent 50 may include aperture 59 in tip 58 that communicates with bore 62, so that when the stent is deployed in myocardium aperture 59 permits flow through bore 62 to pass into an epicardial artery.

Blood entering bore 62 from the left ventricle enters through flange 56, flows through the bore toward sharpened tip 58, and exits into the myocardium through apertures 64. To promote myocardial angiogenesis, stent 50 is preferably coated on either interior surface 66 or exterior surface 54 with a layer of bioactive agent, as described hereinabove. If optional aperture 59 is also included, the flow through bore 62 may pass into an epicardial artery.

Barbs 60 may comprise wire members, for example, welded to stent 50, that collapse when stent 50 is advanced in the distal direction (i.e., into tissue), but are biased to expand against movement in the proximal direction. Following implantation, barbs 60 extend radially outward from exterior surface 54 to secure stent 50 inside the myocardium and prevent the stent from being ejected into the left ventricle. Although FIG. 6B illustrates four barbs 60, it will be understood by those of ordinary skill in the art that one or more barbs may be used to satisfactorily secure stent 50 in the myocardium.

With respect to FIGS. 7A through 8B, stent 70 is described. Stent 70 comprises tubular body 72, exterior surface 74, proximal tines 76 extending from distal endface 78, conical tip 80, and distal tines 82 recessed in slots 84. Bore 86 extends within stent 70 from distal endface 78 to conical tip 80. Conical tip 80 may, or may not, include an opening that communicates with bore 86. Apertures 88 and slots 84 enable exterior surface 74 to communicate with bore 86, thereby permitting fluid communication between the interior and exterior of stent 70. Tubular body 72 may be coated on either the interior surface or exterior surface 74 with a layer of bioactive agent.

Figures 7A, 7B, 8A, 8B:
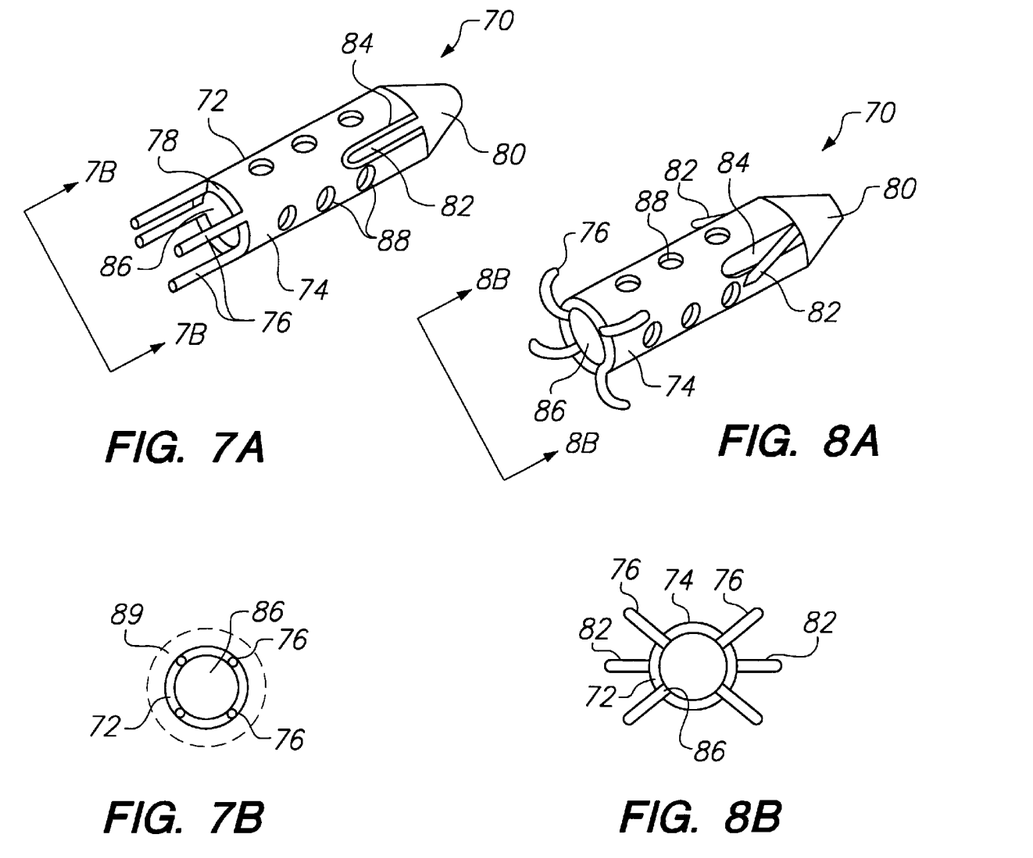
FIGS. 7A and 7B are, respectively, a perspective view and end view, along view line 7B—7B, of an alternative embodiment of a stent of the present invention in a contracted delivery state.
FIGS. 8A and 8B are, respectively, a perspective view and end view, along view line 8B—8B, of the stent of FIGS. 7A and 7B, in a deployed state.

Distal tines 82 may, for example, comprise wire members welded to stent 70 or may be cut from tubular body 72 when forming slots 84. Distal tines 82 bend within slots 84 when stent 70 is advanced in the distal direction (i.e., into tissue), as illustrated in FIG. 7A, but are biased to deflect radially outward out of slots 84 to engage tissue, thereby resisting movement in the proximal direction, as illustrated in FIG. 8A.

Proximal tines 76 preferably comprise a thermally-activated or pseudo-elastic material, such as a nickel-titanium alloy. Proximal tines 76 have a contracted delivery state, as shown in FIG. 7A, in which they extend parallel to, and in-line with, tubular body 72 (for example, when constrained by delivery sheath 89 shown in dotted line in FIG. 7B). When stent 70 is ejected from the delivery sheath (or the sheath is withdrawn proximally while the stent is held stationary), proximal tines 76 expand radially outward to engage the tissue surface. Thus, for example, in FIGS. 8A and 8B, proximal tines 76 extend radially outward to contact the endocardial surface, thereby preventing further motion in the distal direction.

Accordingly, proximal tines 82 secure stent 70 within the myocardium and prevent the stent from being ejected into the left ventricle, while proximal tines 76 prevent the stent from being urged further into the myocardium by wall motion of the heart. Stent 70 perfuses the myocardium via bore 86 and apertures 88 and slots 84. While FIGS. 7 and 8 illustrate four proximal tines 76 and two distal tines 82, it will be understood by those of ordinary skill in the art that different numbers of such tines may be used to satisfactorily secure stent 70 in the myocardium.

Figures 9, 10:
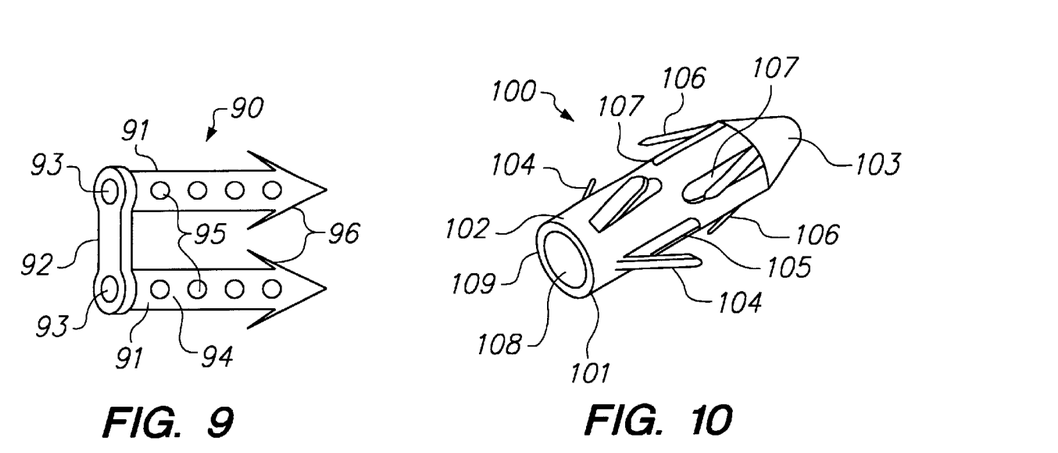
FIG. 9 is a perspective view of a further alternative embodiment of a stent constructed in accordance with the principles of the present invention.
FIG. 10 is a perspective view of still another alternative embodiment of a stent constructed in accordance with the principles of the present invention, in a deployed state.

In FIG. 9, yet another alternative embodiment of a stent constructed in accordance with the present invention is described. Stent 90 includes first and second tubular members 91 connected by strap 92. Each of tubular members 91 is similar in construction to stent 50 of FIG. 6A, and includes a bore 93 that communicates with exterior surface 94 via apertures 95, and includes barbs 96. Strap 92 couples tubular members 91 to one another and provides further assurance that tubular members 91 will not become dislodged from the tissue and also that the tubular members will not be urged further into the tissue by wall motion of the heart. Alternatively, stent 90 may be formed by bending a hollow, apertured tube into a U-shape to form a staple-like structure.

Referring to FIG. 10, a still further alternative embodiment of a stent constructed in accordance with the present invention is described. Stent 100 comprises tubular body 101 having exterior surface 102, conical tip 103, proximal tines 104 recessed in slots 105 and distal tines 106 recessed in slots 107. Bore 108 extends from distal endface 109 to conical tip 103. Slots 105 and 107 enable exterior surface 102 to communicate with bore 108, thereby permitting fluid communication between the interior and exterior of the stent. Tubular body 101 may be coated on either the interior surface or exterior surface 102 with a layer of bioactive agent, as described hereinabove.

Distal and proximal tines 104 and 106 may, for example, comprise wire members welded to stent 100, or may be cut from tubular body 101 when forming slots 105 and 107, respectively. Distal and proximal tines 104 and 106 bend within slots 105 and 107, respectively, when stent 100 is disposed within a delivery sheath, but are biased to deflect out of slots 105 and 107 to engage the tissue and to resist movement when implanted.

Stent 100 may be implanted, for example, using the delivery system described hereinafter with respect to FIGS. 12A and 12B. That delivery system includes a delivery sheath, push tube and guide wire. In particular, stent 100 may be loaded on the guide wire so that the proximal end of the stent is in engagement with the push tube, and so that conical tip 103 extends from the distal end of the sheath. The stent and catheter are urged against the tissue in which the stent is to be implanted, so that the distal end of the catheter enters the tissue to a predetermined depth. The delivery sheath then is withdrawn proximally while the stent is held stationary using the push tube. Once the delivery sheath is withdrawn, proximal and distal tines 104 and 106 expand radially outward to secure the stent in position.

Figure 11A:
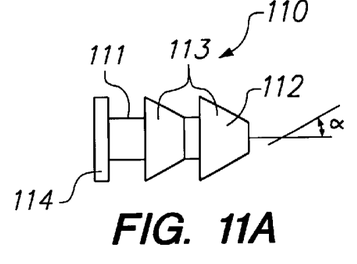
FIGS. 11A and 11B are, respectively, a side view and an end view of a further alternative embodiment of a stent constructed in accordance with the present invention.
Figure 11B:
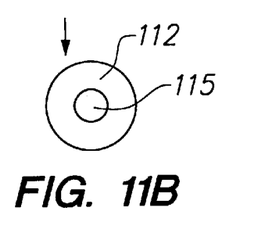

Referring now to FIGS. 11A and 11B, yet another alternative embodiment of a stent constructed in accordance with the principles of the present invention is described. Stent 110 comprises tubular body 111 having exterior surface 112, a plurality of conical ribs 113, flange 114 and bore 115. Stent 110 may optionally include a series of apertures, not shown, that extend from bore 115 to the lateral exterior surface 112. The conical rib on the distal-most endface of stent 110 forms an angle α sufficient to pierce tissue when a distally-directed force is applied to flange 114.

Stent 110 preferably is molded from a bioresorbable material, and is either impregnated or coated with a bioactive agent, as described hereinabove. The distal-most conical rib 113 assists in implanting stent 110, while the proximal faces of the stent prevent it from being ejected into the left ventricle. Flange 114 abuts against the endocardium, when stent 110 is implanted, and prevents further movement of the stent into the myocardium resulting from muscle contraction.

Figure 12A:
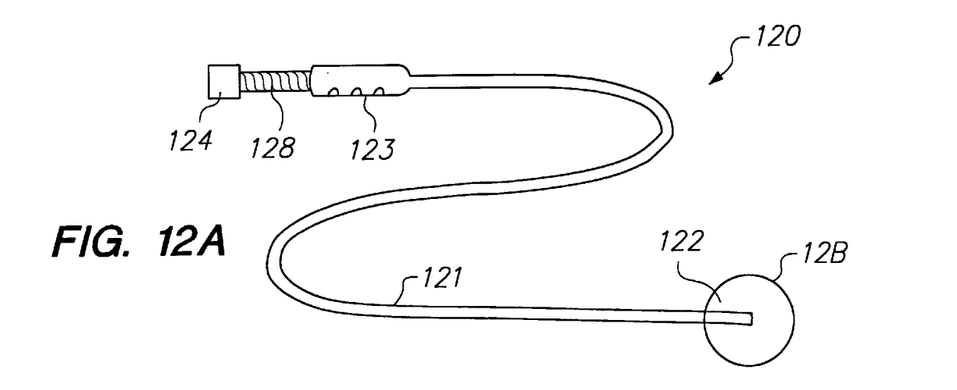
FIGS. 12A and 12B are, respectively, a view of another illustrative delivery system and a sectional side view of a distal end of that delivery system.
Figure 12B:
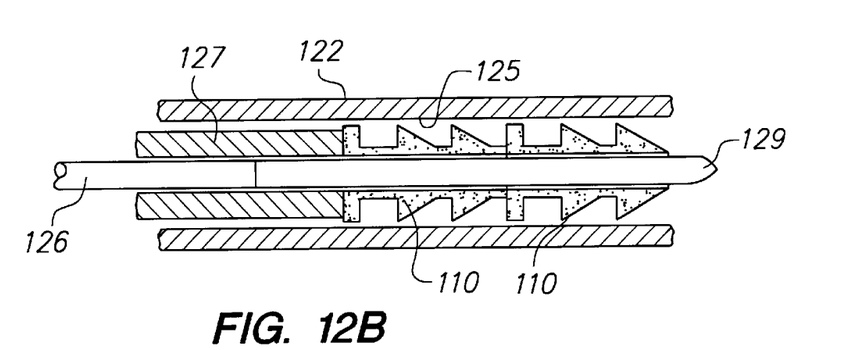

Referring now to FIGS. 12A and 12B, a delivery system for implanting a series of stents 110 in vessel or organ wall is described. Delivery system 120 comprises catheter 121 having distal end 122, first handle portion 123 and second handle portion 124. Delivery system 120 may in addition include a series of stabilization members as described hereinabove for the embodiment of FIGS. 4A and 4B.

As shown in FIG. 12B, distal end 122 of catheter 121 has lumen 125 within which a plurality of stents 110 are engaged end-to-end on wire 126. Push tube 127 engages the proximal face of the proximal-most stent 110 on wire 126, and is engaged at its distal end to second handle portion 124. Second handle portion 124 is engaged in first handle portion 123 by threads 128, so that one rotation of second handle portion 124 relative to first handle portion 123 causes push tube 127 to move distally a predetermined distance.

Wire 126 passes through bores 115 of the plurality of stents 110, so that stents 110 may be translated along wire 126 by distal movement of push tube 127. To prevent inadvertent loss of stents 110 from the distal end of wire 126, it may be preferable that stents 110 frictionally engage wire 126 with a force that is overcome by push tube 127. Wire 126 includes sharpened tip 129 that assists in piercing tissue to permit implantation of stents 110. Delivery system 120 comprises materials typically employed in catheter manufacture, as described hereinabove.

Delivery system 120 may be inserted into the left ventricle, either percutaneously or intraoperatively, using techniques that are per se known. During insertion of delivery system 120 to a treatment site, the delivery system is manipulated using first handle portion 123, while second handle portion 124 remains in the proximal-most position.

Once distal end 122 of catheter 121 has been disposed at a desired implantation site, for example, as determined by fluoroscopy, first handle portion 123 is urged in the distal direction so that sharpened tip 129 of wire 126 pierces the endocardium. Second handle portion 124 is then rotated a predetermined number of times relative to first handle portion 123 (which is held stationary) so that push tube 127 is translated distally. Push tube 127, in turn, urges one of stents 110 along wire 126 so that the stent becomes implanted in the passage formed by the distal end of wire 126.

In particular, threads 128 may be arranged so that the a predetermined number of rotations of the second handle portion causes stent 110 to become fully implanted, and the next stent 110 in the stack is exposed for implantation at a subsequent implantation site. Delivery system 120 is then retracted proximally and repositioned to a new implantation site. When fully implanted, flange 114 of stent 110 abuts against the endocardium, while conical ribs 113 prevent movement of the stent in a proximal direction. Delivery system 120 advantageously enables a number of stents to be implanted during a single insertion of the delivery system to the treatment site.

Figure 13:
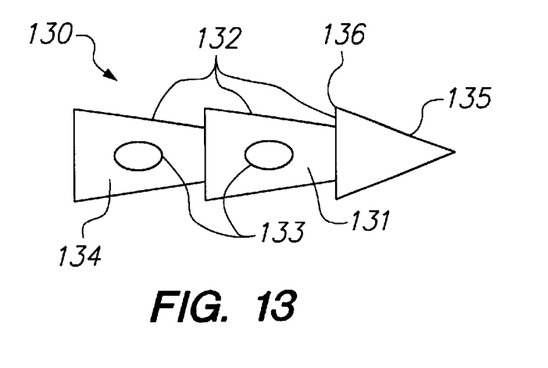
FIG. 13 is a side view of a further alternative embodiment of a stent constructed in accordance with the present invention.

In FIG. 13, a yet further embodiment of a stent constructed in accordance with the present invention is described. Stent 130 comprises body 131 formed of a series of conical sections 132, and includes a bore (not shown) that communicates with apertures 133 in lateral exterior surface 134. Distal-most conical section 132 includes sharpened tip 135.

When implanted in the myocardium, blood from the left ventricle enters the bore through an inlet (not shown) in proximal-most conical section 132, flows through the bore toward sharpened tip 135, and exits into the myocardium through apertures 133 in the manner described hereinabove with respect to the embodiment of FIG. 1. Stent 130 may be constructed as described hereinabove.

Stent 130 may be implanted with a delivery system similar to that described in FIGS. 12A and 12B. Instead of having the stents arranged on wire 126, however, stents 130 may be stacked within the lumen of a catheter in a nested fashion, i.e., so that tip 135 of one stent is engaged in the inlet of the bore of the next distal-most stent in the stack. The proximal-most stent in the stack engages a push tube which may be similar in construction to push tube 127 of delivery system 120.

To prevent the stents from falling out inadvertently, for example, while positioning the delivery system, edges 136 of the stents may be frictionally engaged with the inner surface of the lumen with a force that is sufficiently low to be overcome by the push tube. In this manner, a series of stents may be implanted at selected positions within a vessel or organ wall, without having to repeatedly reload the delivery system.

With respect to FIGS. 14A to 14D, a yet further alternative embodiment of a stent of the present invention is described. Stent 140 comprises a tubular member 141 having spring-biased barbs 142 and 143 and sharpened tip 144. Tubular member 141 may include a bore (not shown) extending from its proximal to distal ends to enhance perfusion. Tubular member 141 preferably comprises a bioresorbable material, such as described hereinabove, and preferably is impregnated with a bioactive substance to stimulate revascularization and/or tissue regeneration.

Figure 14A:
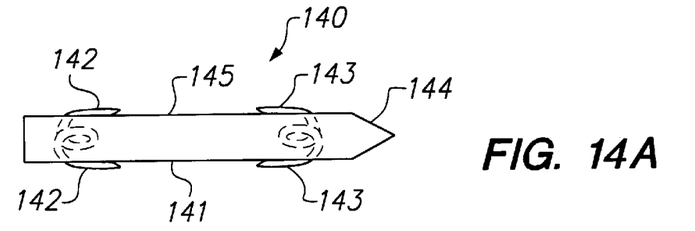
FIGS. 14A and 14B are side views of still another embodiment of a stent constructed in accordance with the present invention in a contracted delivery state and deployed state, respectively.
Figure 14B:
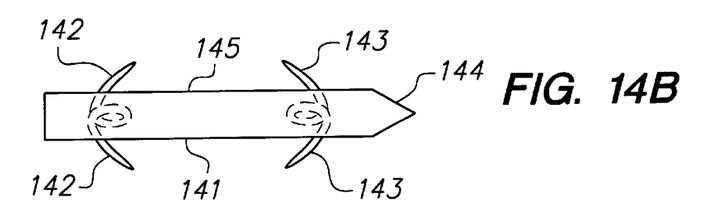

Barbs 142 and 143 preferably have a contracted delivery state, wherein the ends of the barbs lie parallel to (or recessed in) exterior surface 145 of the stent, as shown in FIG. 14A, and a deployed state, wherein the ends of the barbs extend radially outward, as shown in FIG. 14B. Barbs 142 and 143 preferably are arranged with the free ends directed in opposing relation, so as to secure stent 140 against movement once implanted. Stents 140 may be implanted percutaneously, for example, using the delivery system of FIGS. 12A and 12B.

Figure 14C:
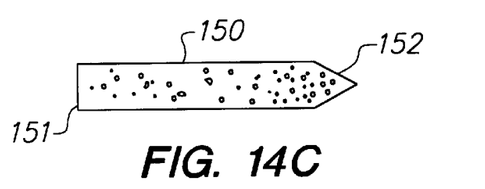
FIGS. 14C and 14D are, respectively, side and end views of a component suitable for use in the stent of FIGS. 14A and 14B.

In FIG. 14C, tubular member 150 suitable for use in constructing stent 140 has a physical or chemical property that varies along the length of the member from proximal end 151 to distal end 152, as indicated by the density of the shading in FIG. 14C. For example, tubular member 150 may be biodegradable, and have a lower density at the proximal end than at the distal end, so that the tubular member erodes in the direction shown by arrow A. Alternatively, tubular member 150 may be impregnated with a drug, or other bioactive agent, that elutes in a higher concentration from the distal end of the tubular member than from the proximal end.

Figure 14D:
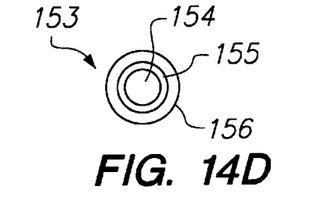

In FIG. 14D, stent 153 having a tubular member similar to that of stent 140 of FIGS. 14A and 14B is shown in cross-section. Instead of having a property that varies as a function of length, like the embodiment of FIG. 14C, stent 153 has a property that varies as a function of radial thickness. Specifically, stent 153 comprises three concentric layers of different growth factors 154, 155 and 156, respectively. Stent 153, which preferably comprises a bioerodible or elutable material, therefore enables a sequence of bioactive agents to be delivered to myocardial tissue over a period of time.

Figure 15:
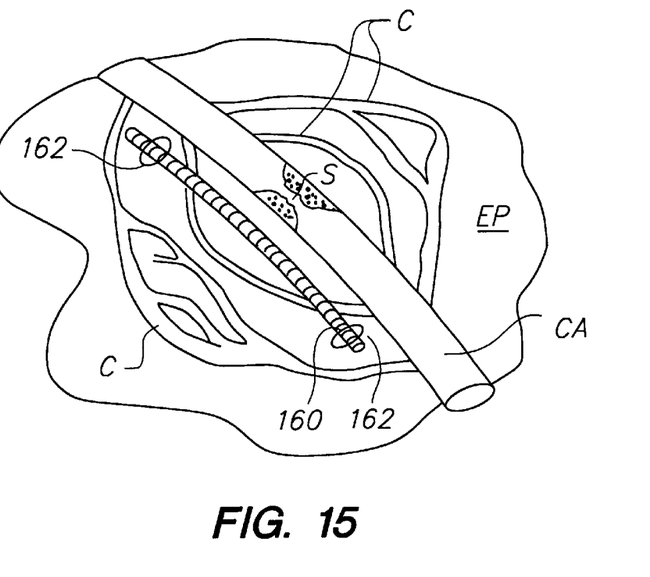
FIG. 15 is a perspective view illustrating a method of implanting yet another embodiment of a stent of the present invention to stimulate revascularization.

Referring now to FIG. 15, a further alternative embodiment of the stent of FIGS. 14 is described for intraoperative use. Stent 160 comprises tubular member 160 formed of a bioresorbable material, and impregnated with a bioactive agent. Stent 160 may have a length of from 3 to 100 mm, and is expected to stimulate revascularization when intraoperatively implanted adjacent to a stenosed artery.

In particular, during an intraoperative procedure, for example, a bypass grafting procedure, a channel first is formed in epicardium EP at a position adjacent to cardiac artery CA having stenosis S. Stent 160 is then inserted into the channel, and may be secured with sutures 162. Stent 160 elutes a bioactive agent, such as described hereinabove, into the surrounding tissue. It is expected that the bioactive agent will encourage revascularization, including the growth of new networks of capillaries C, that provide blood to the tissue downstream of stenosis S.

Although preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed is:

1. A method of implanting a plurality of stents within myocardial tissue to enhance perfusion therein, comprising:

providing a plurality of stents, each stent comprising a tubular member having first and second ends, the first end configured to pierce myocardial tissue, and means for retaining the tubular member within the myocardial tissue;

providing a delivery system comprising a catheter having a lumen;

mounting the plurality of stents in an end-to-end arrangement within the catheter;

positioning the first end of a distal-most one of the plurality of stents at a first desired implantation site;

piercing the myocardial tissue with at least the first end of the stent by applying force to the second end of the stent, thereby ejecting the stent from the catheter and implanting the stent within the myocardial tissue;

engaging the means for retaining with the myocardial tissue to retain the stent in position; and repositioning the catheter at successive desired implantation sites to implant successive ones of the plurality of stents.

2. The method as defined in claim 1 further comprising: stimulating revascularization or tissue regeneration using a bioactive agent eluted from the plurality of stents.

3. The method as defined in claim 1 wherein each tubular member further comprises a flange projecting from the second end, the method further comprising:

when the flange abuts against an endocardial tissue surface, ceasing application of force to the second end of the stent.

4. The method as defined in claim 1 wherein positioning the first end of a distal-most one of the plurality of stents at a first desired implantation site comprises:

inserting the delivery system percutaneously to position the first end of a distal-most one of the plurality of stents at the first desired implantation site.

5. The method as defined in claim 4 wherein the tubular member comprises a bore having an inlet end and an outlet end, and wherein implanting the stent within the myocardial tissue causes the outlet end to pierce an epicardial artery, so that blood passes through the bore from a cardiac chamber and into the epicardial artery.

6. The method as defined in claim 1 wherein positioning the first end of a distal-most one of the plurality of stents a first desired implantation site comprises:

inserting the delivery system intraoperatively to position the first end of a distal-most one of the plurality of stents at an implantation site.

* * * * *